(12) United States Patent
Lareau

(10) Patent No.: US 8,328,760 B2
(45) Date of Patent: Dec. 11, 2012

(54) OCCLUSION RESISTANT CATHETER

(75) Inventor: Raymond Lareau, Westford, MA (US)

(73) Assignee: Angiodynamics, Inc., Latham, NY (US)

( * ) Notice: Subject to any disclaimer, the term of this patent is extended or adjusted under 35 U.S.C. 154(b) by 311 days.

(21) Appl. No.: 12/685,033

(22) Filed: Jan. 11, 2010

(65) Prior Publication Data

US 2011/0172642 A1    Jul. 14, 2011

(51) Int. Cl.
*A61M 5/178* (2006.01)

(52) U.S. Cl. ..................... 604/164.05; 604/30

(58) Field of Classification Search ............ 604/30, 604/164.05, 164.01, 523
See application file for complete search history.

(56) References Cited

U.S. PATENT DOCUMENTS

| | | | |
|---|---|---|---|
| 3,094,124 A | 6/1963 | Birtwell | |
| 3,438,375 A | 4/1969 | Ericson | |
| 3,978,157 A | 8/1976 | Bottenbruch et al. | |
| 4,054,139 A | 10/1977 | Crossley | |
| 4,142,525 A | 3/1979 | Binard et al. | |
| 4,403,983 A | 9/1983 | Edelman et al. | |
| 4,423,740 A * | 1/1984 | Castle et al. | 600/561 |
| 4,468,224 A | 8/1984 | Enzmann et al. | |
| 4,469,483 A | 9/1984 | Becker et al. | |
| 4,483,688 A | 11/1984 | Akiyama | |
| 4,563,180 A | 1/1986 | Jervis et al. | |
| 4,569,673 A | 2/1986 | Tesi | |
| 4,592,920 A | 6/1986 | Murtfeldt | |
| 4,603,152 A | 7/1986 | Laurin et al. | |
| 4,623,327 A | 11/1986 | Mahurkar | |
| 4,769,005 A | 9/1988 | Ginsburg et al. | |
| 4,902,503 A | 2/1990 | Umemura et al. | |
| 4,944,726 A | 7/1990 | Hilal et al. | |
| 5,019,096 A | 5/1991 | Fox et al. | |
| 5,059,170 A | 10/1991 | Cameron | |
| 5,125,893 A | 6/1992 | Dryden | |
| 5,133,742 A | 7/1992 | Pinchuk | |
| 5,151,231 A | 9/1992 | Lambert et al. | |
| 5,205,834 A | 4/1993 | Moorehead et al. | |
| 5,229,431 A | 7/1993 | Pinchuk | |
| 5,249,598 A | 10/1993 | Schmidt | |
| 5,300,048 A | 4/1994 | Drewes et al. | |
| 5,374,245 A | 12/1994 | Mahurkar | |
| 5,403,291 A | 4/1995 | Abrahamson | |
| 5,405,340 A | 4/1995 | Fageol et al. | |
| 5,472,417 A | 12/1995 | Martin et al. | |

(Continued)

FOREIGN PATENT DOCUMENTS

DE    20208420    10/2002

(Continued)

OTHER PUBLICATIONS

Carbothane MSDS from Microspecorporation.com accessed Thursday Aug. 4, 2011. http://www.microspecorporation.com/materials.php?id=5 (1 page).

(Continued)

*Primary Examiner* — Kevin C Sirmons
*Assistant Examiner* — Deanna K Hall
(74) *Attorney, Agent, or Firm* — Ryan D. Artis

(57) ABSTRACT

Catheters configured to minimize, prevent, disrupt, and/or treat thrombus accumulation and subsequent occlusion are disclosed. Such catheters include at least one sidewall cut extending to the catheter distal end that forms catheter sidewall portions that move relative to each other when subjected to a force greater than a threshold force.

15 Claims, 3 Drawing Sheets

U.S. PATENT DOCUMENTS

| | | | |
|---|---|---|---|
| 5,509,897 | A | 4/1996 | Twardowski et al. |
| 5,542,937 | A | 8/1996 | Chee et al. |
| 5,569,182 | A | 10/1996 | Twardowski et al. |
| 5,575,769 | A | 11/1996 | Vaillancourt |
| 5,614,136 | A | 3/1997 | Pepin et al. |
| 5,662,913 | A | 9/1997 | Capelli |
| 5,683,640 | A | 11/1997 | Miller et al. |
| 5,725,510 | A | 3/1998 | Hartmann et al. |
| 5,800,414 | A | 9/1998 | Cazal |
| 5,843,161 | A | 12/1998 | Solovay |
| 5,879,499 | A | 3/1999 | Corvi |
| 5,928,174 | A | 7/1999 | Gibbins |
| 6,033,393 | A | 3/2000 | Balbirz et al. |
| 6,093,180 | A | 7/2000 | Elsberry |
| 6,177,522 | B1 | 1/2001 | Brady et al. |
| 6,197,846 | B1 | 3/2001 | Cmbe et al. |
| 6,200,338 | B1 | 3/2001 | Solomon et al. |
| 6,217,566 | B1 | 4/2001 | Ju et al. |
| 6,227,200 | B1 | 5/2001 | Crump et al. |
| 6,280,423 | B1 | 8/2001 | Davey et al. |
| 6,315,789 | B1 | 11/2001 | Cragg |
| 6,355,858 | B1 | 3/2002 | Gibbins |
| 6,368,658 | B1 | 4/2002 | Schwarz et al. |
| 6,375,637 | B1 | 4/2002 | Campbell et al. |
| 6,409,700 | B1 | 6/2002 | Siegel, Jr. et al. |
| 6,442,415 | B1 | 8/2002 | Bis et al. |
| 6,446,671 | B2 | 9/2002 | Armenia et al. |
| 6,517,520 | B2 | 2/2003 | Chang et al. |
| 6,530,951 | B1 | 3/2003 | Bates et al. |
| 6,545,097 | B2 | 4/2003 | Pinchuk et al. |
| 6,595,966 | B2 | 7/2003 | Davey et al. |
| 6,605,751 | B1 | 8/2003 | Gibbins et al. |
| 6,777,466 | B2 | 8/2004 | Eckstein et al. |
| 6,819,951 | B2 | 11/2004 | Patel et al. |
| 6,897,349 | B2 | 5/2005 | Gibbins et al. |
| 6,938,668 | B2 | 9/2005 | Whicher et al. |
| 7,179,849 | B2 | 2/2007 | Terry |
| 7,264,858 | B2 | 9/2007 | Belliveau et al. |
| 7,410,602 | B2 | 8/2008 | Davey et al. |
| 2001/0037065 | A1 | 11/2001 | Graf et al. |
| 2002/0082559 | A1 | 6/2002 | Chang et al. |
| 2002/0091362 | A1 | 7/2002 | Maginot et al. |
| 2002/0156430 | A1* | 10/2002 | Haarala et al. ............... 604/247 |
| 2003/0065355 | A1 | 4/2003 | Weber |
| 2003/0203991 | A1 | 10/2003 | Schottman et al. |
| 2004/0068241 | A1 | 4/2004 | Fischer, Jr. |
| 2004/0068251 | A1 | 4/2004 | Chan et al. |
| 2004/0068315 | A1 | 4/2004 | Chandrasekaran et al. |
| 2004/0073171 | A1 | 4/2004 | Rogers et al. |
| 2004/0076582 | A1 | 4/2004 | DiMatteo et al. |
| 2004/0131863 | A1 | 7/2004 | Belliveau et al. |
| 2004/0171747 | A1 | 9/2004 | Zhong |
| 2004/0199128 | A1 | 10/2004 | Morris et al. |
| 2004/0220534 | A1 | 11/2004 | Martens et al. |
| 2004/0266301 | A1 | 12/2004 | Vedula et al. |
| 2005/0010275 | A1 | 1/2005 | Sahatjian et al. |
| 2005/0013988 | A1 | 1/2005 | Fu et al. |
| 2005/0119724 | A1 | 6/2005 | Phaneuf et al. |
| 2005/0131356 | A1 | 6/2005 | Ash et al. |
| 2005/0182352 | A1 | 8/2005 | DiMatteo et al. |
| 2005/0192546 | A1 | 9/2005 | Grieg et al. |
| 2005/0216074 | A1 | 9/2005 | Sahatjian et al. |
| 2006/0004325 | A1 | 1/2006 | Hamatake et al. |
| 2006/0052757 | A1 | 3/2006 | Fischer et al. |
| 2006/0189922 | A1 | 8/2006 | Amarasinghe et al. |
| 2007/0299043 | A1 | 12/2007 | Hunter et al. |
| 2008/0108975 | A1 | 5/2008 | Appling et al. |
| 2008/0234659 | A1 | 9/2008 | Cheng et al. |
| 2009/0036768 | A1 | 2/2009 | Seehusen et al. |
| 2009/0171319 | A1 | 7/2009 | Guo et al. |
| 2009/0171436 | A1 | 7/2009 | Casanova et al. |
| 2009/0326560 | A1 | 12/2009 | Lampropoulos et al. |

FOREIGN PATENT DOCUMENTS

| | | |
|---|---|---|
| EP | 0328421 | 8/1989 |
| EP | 0589577 | 3/1994 |
| EP | 0987042 | 3/2000 |
| FR | 2718969 | 10/1995 |
| JP | 2001172848 | 6/2001 |
| JP | 2001340466 | 12/2001 |
| JP | 2003037632 | 2/2003 |
| JP | 2006296694 | 11/2006 |
| WO | WO-96/41649 | 12/1996 |
| WO | WO-97/10858 | 3/1997 |
| WO | WO-99/38550 | 8/1999 |
| WO | WO-99/42156 | 8/1999 |
| WO | WO-00/53253 | 9/2000 |
| WO | WO-01/70324 | 9/2001 |
| WO | WO-2006/058042 | 6/2006 |

OTHER PUBLICATIONS

Carbothane MSDS from msds.carboline.com accessed Thursday Aug. 4, 2011. http://msds.carboline.com/website/carbmsds.nsf%28all%29/87496753746CA5888525705A004343CE8/$file/Carbothane+134+HG+PDS+-11.pdf (2 pgs.).

"AgION's Silver Copper Zeolite Okayed by FDA for Food Contact," AgION Technologies, Inc., http://www.agion-tech.com/NewsDetail.asp?PressID=91, 2 pages (2005).

"Anatomy and Placement," http://www.rnceus.com/picc/piccanat.html, 2 pages (2005).

"Application Guide," Spire Corporation, http://www.spirebiomedical.com/Biomedical/app_guide.html, 3 pgs (2005).

"Biocompatibles—Advanced Biomedical Polymers," http://www.pharmaceutical-technology.com/contractors/drug_delivery/biocompatibles, 3 pages (2005).

"Broviac Catheters, PICC Lines and Other Catheters," The American Pediatric Surgical Association, http://www.eapsa.org/parents/catheter.htm, 13 pages (2005).

"Central Venous Catheters," http://academic.luzerne.edu/nfrusciante/nur204/powerpoints/cvc.pdf, 11 pages (2005).

"Description of Ion Beam Assisted Deposition Process," Spire Corporation, http://www.spirebiomedical.com/Biomedical/ionbeam.html, 2 pages (2005).

"Description of Ion Implantation Process," Spire Corporation, http://www.spirebiomedical.com/Biomedical/ionimpl.html, 4 pages (2005).

"Echo-Coat Ultrasound Needles," The 2001 Medical Design Excellence Awards, http://www.devicelink.com/expo/awards02/stsbiopolymers.html, 2 pages (retrieved from the internet prior to the filing of the application).

"Electrically Ionized Metals for the Prevention of Catheter Colonization with Microorganisms," The University of Texas MD Anderson Cancer Center, Office of Technology Development, http://www.mdanderson.org/departments/techcommerc, 2 pages(2005).

"FAQ: Electroplating—How It Works," http://www.finishing.com/faqs/howworks.html, 4 pages (2005).

"Fighting Infections, Healing Wounds," AcryMed, Inc., http://www.acrymed.com, 1 page (2005).

"Flexima™ Tight Loop All-Purpose Drainage Catheters," Boston Scientific Corporation, http://www.bostonscientific.com, 1 page (2005).

Gibbins, "SilvaGard™ Technology Summary," AcryMed, Inc., http://www.acrymed.com/pdf%20files/bpease_silvgrd.pdf, 8 pages (2006).

Gibbins et al., "The Role of Antimicrobial Silver Nanotechnology," Medical Device & Diagnostic Industry, http://www.devicelink.com/mddi/archive/05/08/005.html, 6 pages (2005).

"Ion Beam Processing (IBP) Technologies—Sector Study," BDM Federal Inc., prepared for the North American Technology and Industrial Base Organization (NATIBO), 133 pages (1996).

"Ion-Sight™," Spire Corporation, http://www.spirebiomedical.com/Biomedical/Ionsight.html, 2 pages (2005).

"Ion-Sight™ Radio-Opaque Coatings for Medical Devices is a State-of-the-Art Metallic Coating Applied to Polymers," 1 page (retrieved from the internet prior to filing of the application).

Management of a PICC Line (Peripherally Inserted Central Catheter), CancerBACUP, http://www.cancerbacup.org.uk/Treatments/Chemotherapy/Linesports/PICCline, 4 pages (2005).

"New Multifunctional Textiles: Antimicrobial Treatments," Intelligent Textile Structures—Application, Production & Testing, International Workshop, Thessaloniki, Greece, Amphitheater of Thessaloniki Technology Park, 31 pages (2005).

Oberst, "Researchers Describe How to Put the 'Nano' in Synthetic Polymers," Cornell Chronicle, http://www.news.cornell.edu/Chronicle/04/6.10.04/CCMR-POP_conf.html, 2 pages (2004).

"ON-Q C-Bloc Continuous Nerve Block System," I-Flow Corporation, http://www.iflo.com/prod_ong_classic.php, 7 pages (2005).

"ON-Q® PainBuster® Post-Op Pain Relief System," I-Flow Corporation, http://www.iflo.com/prod_ong_classic.php, 7 pages (2005).

Powers, "Antimicrobial Silver Nanoparticles Eliminate Biofilm Formation on Medical Devices," NanoBiotech News, vol. 3, No. 30, 2 pages (2005).

"Process Services," Spire Corporation, http://www.spirebiomedical.com/Biomedical/process_serv.html 2 pages (2005).

Rosenthal, "PICC Line," University of Illinois Medical Center at Chicago, http://uimc.discoveryhospital.com/main.php?t=enc&id=3017, 2 pages (2005).

"SilvaGard™ Antimicrobial Surface Treatment,"AcryMed, Inc., http://www.acrymed.com/techATD.htm, 2 pages (2005).

"Silver Catheter Destroys Bacterial Paradise," NewsDesk No. 9820, Siemens AG, http://w4.siemens.de/en2/html/press/newsdesk_archive/1998/e_9820_d.html, 2 pages (1998).

Sobie, "*Ion Beam Technology for Thin Film Applications*," edited from a reprint of Vacuum & Thinfilm, 6 pages (2001).

"SPI-Argent™," Spire Corporation, http://www.spirebiomedical.com/Biomedical/SPIargent.html, 2 pages (2005).

"Tal MicroDrainage™ Set," Boston Scientific Corporation, http://www.bostonscientific.com, 2 pages (2005).

"Technology Overview," Spire Corporation, http://www.spirebiomedical.com/Biomedical/techoverview.html, 1 page (2005).

"Types of CV ADs," Hemophilia Galaxy, http://www.hemophiliagalaxy.com/patients/managing/va_central/types.html 3 pages (2005).

"Vaxcel® Implantable Ports with PASV® Valve Technology," Boston Scientific Corporation, http://www.bostonscientific.com, 3 pages (2005).

"Vaxcel® Implantable Ports with PASV® Valve Technology—Port Design Options," Image, Boston Scientific Corporation, http://www.bostonscientific.com (2005).

"Vaxcel® Peripherally Inserted Central Catheter (PICC)," Boston Scientific Corporation, http:www.bostonscientific.com, 3 pages (2005).

"Vaxcel® Peripherally Inserted Central Catheter (PICC)—Instructions for Use," Boston Scientific Corporation, http://www.bostonscientific.com, 3 pages (2005).

"Vaxcel® Peripherally Inserted Central Catheter (PICC)—Product Information" Boston Scientific Corporation, http://www.bostonscientific.com, 3 pages (retrieved from the internet prior to the filing of the application).

"Vaxcel® Plus Chronic Dialysis Catheter," Boston Scientific Corporation, http://www.bostonscientific.com, 2 pages (2005).

"Vaxcel® Tunneled Central Venous Catheter," Boston Scientific Corporation, http://www.bostonscientific.com, 5 pages (2005).

"Vaxcel® Tunneled Central Venous Catheters—Product Information," Boston Scientific Corporation, http://www.bostonscientific.com, 3 pages (retrieved from the internet prior to filing of the application).

"Venous Access Device Insertion and Maintenance," Boston Scientific Corporation, http://www.bostonscientific.com/templatedata/imports/HTML/infusion_therapy/index.html, 1 page (2005).

Zschaler, "Testing of the Antimicrobial Effect of Catheter Tubing with a Roll Culture Method," 4 pages (2005).

Hunter et al., "Anti-Scarring Drug Combinations and Use Thereof," U.S. Appl. No. 60/723,053 Specification (2005).

J.A. Zawacki, "Carbothane Fixed Split-Tip Dialysis Catheters for Longer-Term Haemodialysis," Business Briefing: Global Healthcare—Advanced Medical Technologies, pp. 1-2 (2004).

Thermedics Polymer Products, Committed to Providing Medical Grade Thermoplastic Polyurethane Resins, http://www.viasys.tv/prod_serv/downloads/139_Brochure.pdf, pp. 1-8 (2005).

"HemoSplit Catheter, 510(k), Summary of Safety and Effectiveness, 21 CFR 807.92(a)," (2003).

"Noveon, Medical Urethanes," http://www.estane.com/technology/Medical.asp, pp. 1-6 (2005).

"Vaxcel® Plus Chronic Dialysis Catheter," http://www.bostonscientific.com/med_specialty/deviceDetail.jsp?task=tskBasicDevice.isp&sectionId=4&re1ID=4,178,179,180&deviceId=13015&uniqueId=MPDB3839, (2007).

T.M. Vesely, "Tunneled Catheter Design: Does it Matter? (Lecture)," The Journal of Vascular Access, vol. 6, pp. 132-136 (2005).

Asch, "Venous access: options, approaches and issues," Can Assoc. Radiol J., vol. 52, No. 3 pp. 153-164 (2001).

Herts et al., "Power injection of contrast media using central venous catheters: feasibility, safety, and efficacy," AJM Am. J. Roentgenol., vol. 176, No. 2, pp. 447-453 (2001).

Roth et al., "Influence of radiographic contrast media viscosity to flow through coronary angiographic catheters," Cathet. Cardiovasc. Diagn., vol. 22, No. 4, pp. 290-294 (1991).

Carlson et al., "Safety considerations in the power injection of contrast media via central venous catheters during computered tomogrphic examinations," Invest. Radiol., vol. 27, No. 5, p. 337-340 (1992).

Kaste et al., "Safe use of powr injectors with central and peripheral venous access devices for pediatric CT," Pediatr. Radiol., vol. 26, No. 8, pp. 449-501 (1996).

Herts et al., "Power injection of intravenous contrast material through central venous catheters for CT: in vitro evaluation," Radiology, vol. 200, No. 3, pp. 731-735 (1996).

Rivitz et al., "Power injection of peripherally inserted central catheters," J. Vasc. Interv. Radiol., vol. 8, No. 5, pp. 857-863 (1997).

Rogalla et al., Safe and easy power injection of contrast material through a central line, Eur. Radiol., vol. 8, No. 1, pp. 148-149 (1998).

Williamson et al., "Assessing the adequacy of peripherally inserted central catheters for power injection of intravenous contrast agents for CT," J. Comput. Assist. Tomogr., vol. 25, No. 6, pp. 932-937 (2001).

Chahoud et al., "Randomized comparison of coronary angiography using 4F catheters: 4F manual versus 'Acisted' power injection technique," Catheter Cardiovasc. Interv., vol. 53, No. 2, pp. 221-224 (2001).

Walsh et al., "Effect of contrast agent viscosity and injection flow velocity on bolus injection pressures for peripheral venous injection in first-pass myocardial perfusion studies," Technol. Health Care, vol. 10, No. 1, pp. 57-63 (2002).

Saito et al., "Diagnostic brachial coronary arteriography using a power-assisted injector and 4 French catheters with new shamps," J. Invasive Cardiol., vol. 9, No. 7, pp. 461-468 (1997).

* cited by examiner

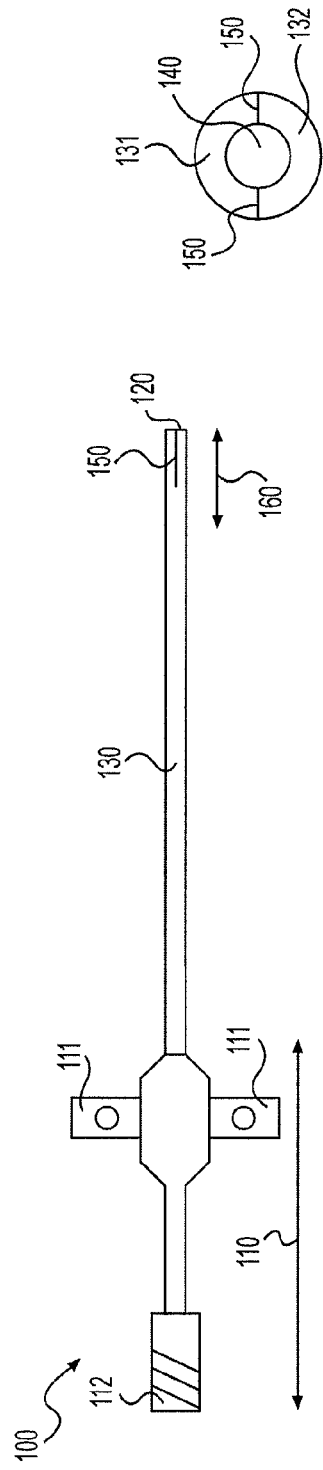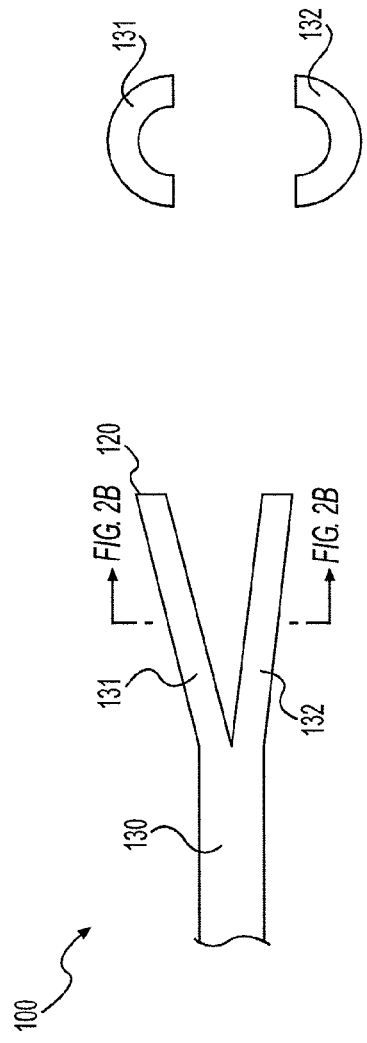

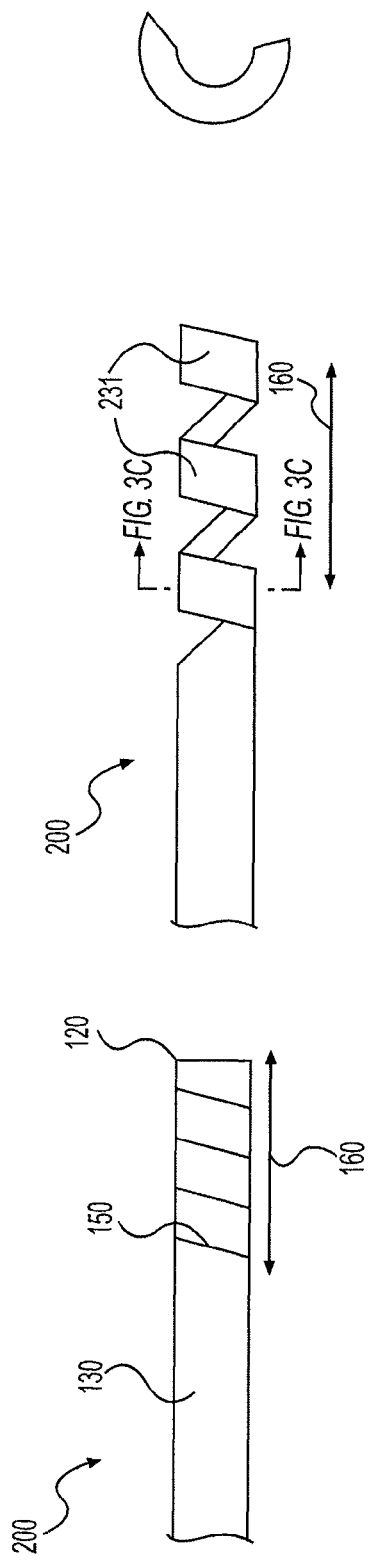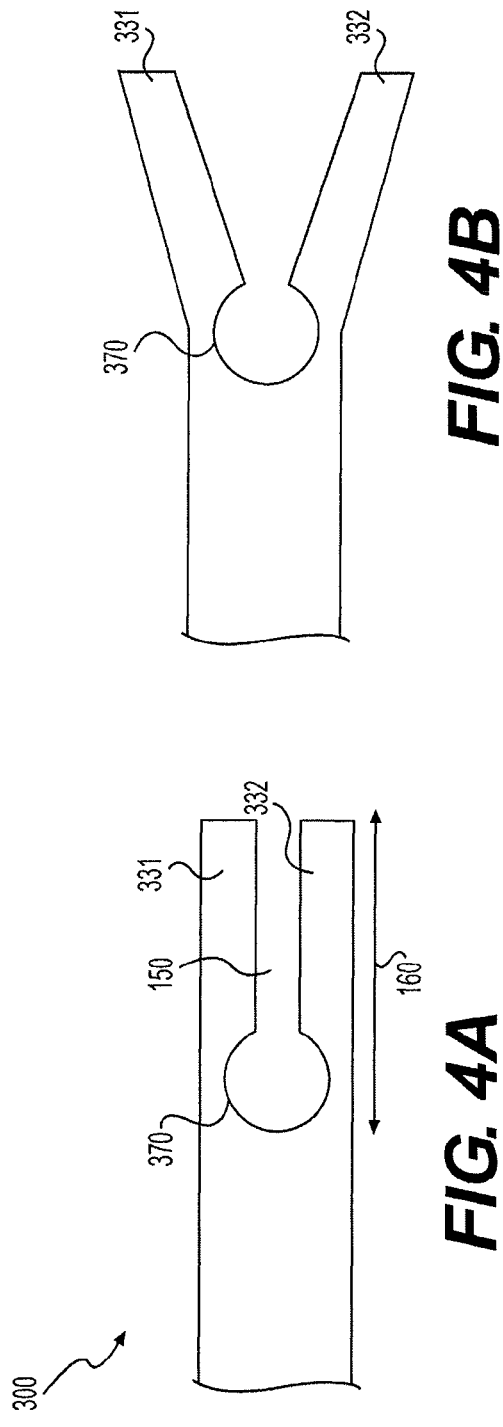

OCCLUSION RESISTANT CATHETER

FIELD OF THE INVENTION

The present invention relates to indwelling catheter devices, and more specifically, indwelling catheter devices that minimize, prevent, disrupt, and/or treat catheter occlusion.

BACKGROUND

There are a number of implantable medical devices, such as indwelling catheters, that are used for the repeated and prolonged access to a patient's vascular system, urinary system, or other bodily conduits. Such devices include peripherally-inserted central catheters ("PICC's"), central venous catheters ("CVC's"), dialysis catheters, implantable ports, midline infusion catheters, and drainage catheters. These devices are typically implanted into a patient for an extended period of time to allow for multiple treatments, such as the delivery of therapeutic agents or dialysis treatments. Use of such devices eliminates the need for multiple placements of single-use devices, thus reducing the risk of infection and placement complications, and reducing the overall cost of patient care. Examples of such implantable medical devices include Vaxcel® PICC's and ports, Xcela® PICC's and ports, Vaxcel® Plus Chronic Dialysis catheters, and the Exodus™ drainage catheter (all from Navilyst Medical, Inc., Marlborough, Mass.).

Like any implantable device placed into the bloodstream, PICC's, ports, and other similar indwelling devices are susceptible to occlusion due to factors relating to thrombosis, encrustation, and the like. Catheter occlusion remains one of the most common noninfectious complications of long-term indwelling devices. Such occlusions can result in catheter malfunction, infection, and/or major vessel thrombosis. Thrombotic causes for catheter obstruction include intraluminal thrombus, extraluminal fibrin sleeve, mural thrombus, or major vessel occlusion and present as either complete or partial occlusion. For example, venous catheters may become encased with a fibrin material shortly after placement within a patient. This fibrin sheath is believed to be comprised of fibrin, platelets, and/or a fibrous collagen substance, and can lead to subsequent catheter occlusion.

In other types of indwelling catheters, such as those that are inserted into the urinary system, catheter occlusion may result from infection of the urine by a urease producing bacteria. Such infection may lead to the formation of a thickening biofilm that results in catheter occlusion. Occlusion may also result from the crystallization of salts from bodily fluids onto the catheter. It is estimated that recurrent blockage of urinary catheters occurs in as many as 50% of long-term catheterized patients.

Current techniques used to minimize, prevent, or treat catheter occlusion include flushing the catheter with fluids, such as heparinized saline to prevent thrombus formation, or citric acid to dissolve encrustation. It would be advantageous, however, to provide catheters that include means to minimize, prevent, disrupt, and/or treat occlusion.

SUMMARY OF THE INVENTION

In one aspect, the present invention comprises embodiments of indwelling catheters for inserting into a patient. The catheters comprise a proximal section, a distal end, and a tubular sidewall extending between the proximal and distal ends and defining a lumen for the passage of fluid therethrough. The catheters include at least one cut in the sidewall that extends to the catheter distal end and separates the sidewall into sidewall portions. When the distal end is subjected to a force greater than a threshold force, the sidewall portions move relative to each other to thereby minimize, prevent, disrupt, and/or treat catheter occlusion.

In another aspect, the present invention comprises a method of treating a patient using the catheters of the present invention.

In yet another aspect, the present invention comprises a kit that includes one or more catheters of the present invention.

DESCRIPTION OF THE DRAWINGS

FIGS. 1a and 1b are perspective and end views, respectively, of a catheter according to an embodiment of the present invention that includes two parallel cuts.

FIGS. 2a and 2b are side and cross-sectional views, respectively, showing a distal section of the embodiment of FIG. 1 when fluid passes through the catheter at a pressure greater than a threshold pressure.

FIGS. 3a and 3b are side views, and FIG. 3c is a cross-sectional view, showing a distal section of an embodiment of the present invention that includes a single spiral cut.

FIGS. 4a and 4b are side views of a distal section of a catheter according to an embodiment of the present invention that includes relief cuts.

DESCRIPTION OF THE PREFERRED EMBODIMENTS

Figure 5:
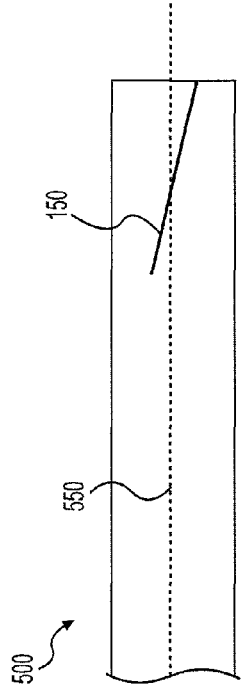
FIG. 5 is a side view of a distal section of a catheter according to an embodiment of the present invention that includes a curved cut.

The present invention provides indwelling catheters that may reside in the vasculature or other bodily lumens of patients for prolonged periods of time. As used herein, the term "indwelling catheter" is intended to include any flexible tube that is placed and left in the body over an extended time period. The catheters of the present invention include a unique design that minimizes, prevents, disrupts, and/or treats occlusion due to thrombus formation, encrustation, or the like.

A catheter according to an embodiment of the present invention is shown in side and cross-sectional views in FIGS. 1a and 1b, respectively. Although an exemplary indwelling catheter is shown in the figures included herein, it should be appreciated that the present invention is applicable to any catheter device that resides within a patient for an extended period of time. Such catheters include PICC's, CVC's, dialysis catheters, infusion catheters, drainage catheters, and any other tubular devices that are inserted into bodily lumens or organs for the delivery and/or withdrawal of fluids.

The catheter 100 illustrated in FIG. 1a includes a proximal section 110, a distal end 120, and a tubular sidewall 130 extending between the proximal section 100 and distal end 120. The proximal section 110 is configured to remain outside of a patient's body when the catheter 100 is in use. For example, the proximal section 110 optionally includes suture wings 111 that are attachable to the skin of a patient via sutures or the like. The proximal section 110 also optionally includes a luer fitting 112 for connection to a fluid source, such as medications, saline, nutrients, and blood. The distal end 120 is configured to be inserted into a patient to reside within any suitable bodily structure, such as a bodily lumen (e.g., a blood vessel, the urethra, the ureter, the esophagus, or the colon) or an organ (e.g., the kidney, the heart, or the stomach). The tubular sidewall 130 extending between the proximal section 110 and distal end 120 defines a lumen 140 for the passage of such fluids to or from the patient.

The catheter 100 includes at least one cut 150 in the tubular sidewall 130 extending from the distal end 120, the length of the cut(s) 150 defining a distal section 160 of the catheter 100. As used herein, the term "cut" is not limited to a discontinuity created by a particular method of manufacture, but rather is intended to be broad enough to include any gap, break, cut, discontinuity, opening, or the like created in the sidewall 130 by any suitable technique. In an exemplary embodiment, the length of the at least one cut 150, and therefore the length of the distal section 160, is within the range of about 1 mm to about 20 mm, and preferably about 1 mm to about 5 mm. The embodiment shown in FIGS. 1a and 1b includes two cuts 150 in the sidewall 130, the two cuts 150 being at about 180 degrees from each other and being substantially parallel to each other and to a longitudinal axis of the lumen 140.

In all embodiments of the invention, the at least one cut 150 extends through to the distal end 120 and separates the sidewall 130 into sidewall portions that move relative to each other due to separation forces, such as internal or external forces, that are greater than a threshold force. An example of such an internal force can result from the passage of fluid through the lumen 140; and an example of such an external force can result from the patient's anatomy, such as a surrounding bodily lumen or tissue such as cyclic forces applied by the superior vena cava.

In the embodiment shown in FIGS. 1a and 1b, the passage of fluid through the lumen 140 at a pressure higher than a threshold pressure results in the application of a force upon the sidewall portions 131 and 132 within the distal section 160 such that they move away from each other, as shown in FIGS. 2a and 2b. Such movement of the sidewall within the distal section 160 is believed to be useful to minimize, prevent, disrupt, and/or treat catheter occlusion by preventing the accumulation of materials that contribute to thrombus or encrustation formation, and/or dislodging any such materials that have already adhered to the catheter on the exterior of the sidewall 130 or within the lumen 140 in the distal section 160.

In another embodiment of the invention as shown in FIGS. 3a-3c, a single cut 150 is made within the sidewall 130 of a catheter 200 and extends as a spiral from the distal end 120 to separate sidewall 140 into sidewall portions 231 as viewed in a single plane. Like the embodiment shown in FIGS. 1 and 2, the passage of fluid through the lumen 140 of catheter 200 at a pressure higher than a threshold pressure causes the application of a force upon the sidewall portions 231 greater than a threshold force such that they move away from each other. In this embodiment, such fluid passage causes the distal section 160 to move by enlargement in a distal and/or radial direction by the separation of sidewall portions 231 that are defined by the spiral cut 150.

Although the embodiments shown in FIGS. 1-3 are shown such that sidewall portions defined by the at least one cut 150 abut each other when not subjected to a force above a threshold force, the present invention includes embodiments such as the embodiment of FIG. 4 in which sidewall portions are separated from each other in an as-manufactured condition and prior to being subjected to any force. It is thus intended that the at least one cut used in the embodiments of the present invention may optionally result in the removal of material from the catheter sidewall to create a distance between sidewall portions. Alternatively, the at least one "cut" may be made by radiofrequency welding or other suitable fabrication technique to leave an as-manufactured separation between sidewall portions, rather than by an actual physical cutting technique.

In the embodiment shown in FIGS. 4a and 4b, the distal section 160 of the catheter 300 includes a cut 150 that separates the sidewall 130 into sidewall portions 331, 332. The as-manufactured separation between the sidewall portions 331, 332 is preferably about 0.001 inches to about 0.060 inches. In a preferred embodiment, the catheter 300 includes a relief cut 370 at the proximal end of the cut 150. The relief cut 370 is preferably semi-circular, and helps to facilitate the movement of sidewall portions 331, 332 when the distal section 160 is subjected to forces greater than a threshold force, as shown in FIG. 4b. Although FIG. 4b and the drawings for other embodiments show sidewall portions moving away from each other, it is within the scope of the present invention that the sidewall portions move towards each other due to the application of external forces to thereby minimize, prevent, disrupt, and/or treat catheter occlusion.

Figure 6:
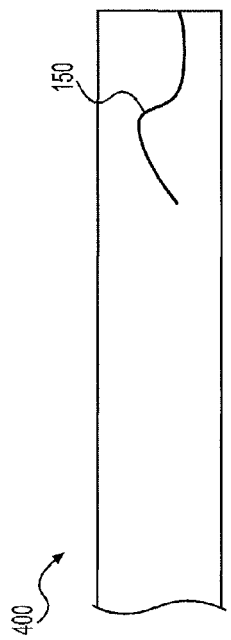
FIG. 6 is a side view of a distal section of a catheter according to an embodiment of the present invention that includes an angled cut.

In other embodiments 400 and 500, the catheters of the present invention include cuts 150 that are curved, as shown in FIG. 5, and/or extend at an angle with respect to a longitudinal axis 550 of the catheter, as shown in FIG. 6. Although the catheters of the present invention are illustrated as including one or two cuts, it should be appreciated that there is no limit to the number of cuts that may be included in the catheters of the present invention, other than ability to manufacture.

Figure 7:
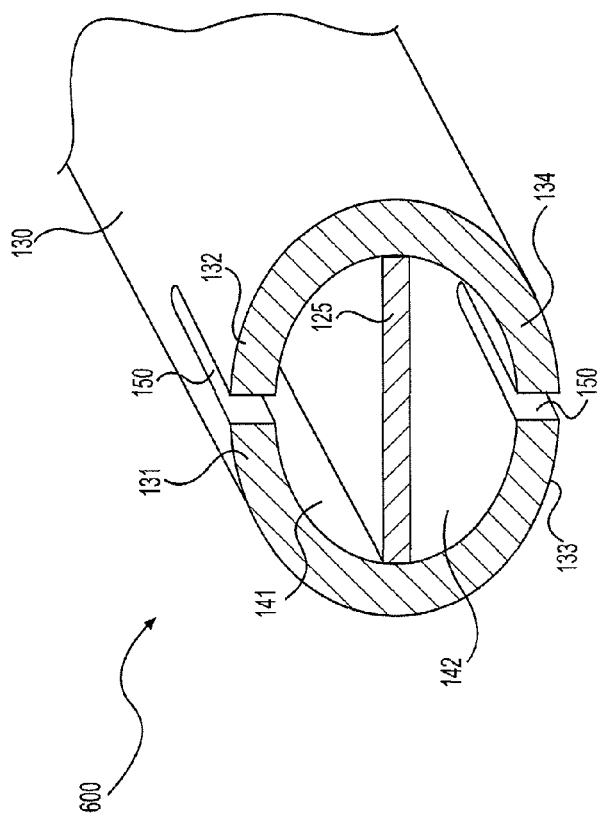
FIG. 7 is an end view of a dual-lumen catheter, according to an embodiment of the present invention.

In one embodiment, the catheter of the present invention is a multi-lumen catheter, such as the dual-lumen catheter 600 shown in FIG. 7. The dual-lumen catheter 400 includes a dividing wall 125 that extends along the length of the catheter and divides it into first and second lumens 141, 142. At least one cut 150 is provided in the sidewall 130 over either or both of the first and second lumens 141, 142. In the embodiment shown in FIG. 7, two cuts 150 are provided in the catheter 400, with a single cut made in the sidewall over each of the first and second lumens 141, 142. When fluid is passed through the first 141 and/or the second 142 lumens at a pressure above a threshold pressure, or alternatively when external forces from the patient's anatomy act upon the distal end of the catheter 600, the respective sidewall portions 131, 132, and/or 133, 134 move relative to each other.

The materials used to fabricate the catheters of the present invention are any suitable polymeric materials as are known in the art, such as thermoplastic polyurethanes, nylons, polyether block amides, ethylene vinyl acetate, silicones, polyolefin elastomers, styrenic elastomers, and polyester elastomers. The catheters are preferably manufactured by extrusion fabrication techniques, as are known in the art. The cuts provided in the catheters of the present invention may be made by any suitable cutting process, by removing sidewall material through micro-milling, radiofrequency welding, or other suitable machining technique, or by molding or extruding the catheters with the cuts in an as-manufactured configuration.

As described herein, the catheters of the present invention include sidewall portions defined by cuts that move relative to each other when the catheter is subjected to internal and/or external forces above a threshold force. As used herein, the term "threshold force" is intended to mean the force required to move at least part of the sidewall portions, as described herein, relative to each other. As such, the threshold force will differ for each catheter, and will depend upon factors such as the composition, thickness, and geometry of the catheter sidewall.

It will be apparent to those skilled in the art that various modifications and variations can be made in the structure and methodology of the present invention. Thus, it is intended that the present invention cover such modifications and variations provided that they come within the scope of the appended claims and their equivalents.

I claim:

1. A catheter for inserting into a patient, comprising:
   a proximal section, a distal end, and a tubular sidewall extending from said proximal section to said distal end and defining a lumen for the passage of fluid;
   a distal section that includes said distal end and a length of said sidewall extending proximally from said distal end; and
   at least one cut in said sidewall in said distal section and extending to said distal end, said at least one cut separating said sidewall into sidewall portions that move relative to each other when at least a portion of said distal section is subjected to a force greater than a threshold force wherein said at least one cut in said sidewall includes a semicircular opening disposed at a terminus of said at least one cut.

2. The catheter of claim 1, wherein said force is caused by fluid passing through said lumen.

3. The catheter of claim 2, wherein said sidewall portions move away from each other when at least a portion of said distal section is subjected to a force higher than a threshold force.

4. The catheter of claim 1, wherein said force is caused by an anatomy of the patient.

5. The catheter of claim 4, wherein said anatomy is the superior vena cava.

6. The catheter of claim 4, wherein said sidewall portions move toward each other when at least a portion of said distal section is subjected to a force higher than a threshold force.

7. The catheter of claim 1, wherein said at least one cut extends substantially parallel with respect to a longitudinal axis of said lumen.

8. The catheter of claim 1, wherein said at least one cut extends from said distal end to said circular opening.

9. The catheter of claim 1, further comprising a dividing wall extending between said proximal section and said distal end, said dividing wall separating said lumen into a first portion and a second lumen portion.

10. The catheter of claim 9, wherein said catheter comprises a first cut in said sidewall and a second cut in said sidewall, said first cut being made in said sidewall over said first portion of said lumen, and said second cut being made in said sidewall over said second portion of said lumen.

11. The catheter of claim 1, wherein said catheter comprises a single cut.

12. The catheter of claim 1, wherein said catheter comprises at least two cuts.

13. The catheter of claim 1, wherein said catheter is a peripherally-inserted central catheter.

14. The catheter of claim 1, wherein said catheter is a drainage catheter.

15. A catheter for inserting into a patient, comprising:
   a proximal section, a distal end, and a tubular sidewall extending from said proximal section to said distal end and defining a lumen for the passage of fluid;
   a distal section that includes said distal end and a length of said sidewall extending proximally from said distal end;
   two cuts in said sidewall in said distal section and extending to said distal end, said two cuts separating said sidewall into sidewall portions that move away from each other when fluid is passed through said lumen at pressures higher than a threshold pressure; and
   two semi-circular openings in said sidewall in said distal section, each semi-circular opening located at a terminus of a cut in the sidewall.

* * * * *